US012758103B2

(12) United States Patent
Gepner et al.

(10) Patent No.: US 12,758,103 B2
(45) Date of Patent: Oct. 13, 2026

(54) APPARATUS AND METHOD FOR CHARACTERIZING ARTERIAL STIFFNESS

(71) Applicants: Wisconsin Alumni Research Foundation, Madison, WI (US); Department of Veterans Affairs, Washington, DC (US)

(72) Inventors: Adam D. Gepner, Madison, WI (US); Ryan Pewowaruk, Madison, WI (US)

(73) Assignees: Wisconsin Alumni Research Foundation, Madison, WI (US); United States Government as Represented by the Department of Veterans Affairs, Washington, DC (US)

( * ) Notice: Subject to any disclaimer, the term of this patent is extended or adjusted under 35 U.S.C. 154(b) by 300 days.

(21) Appl. No.: 18/432,707

(22) Filed: Feb. 5, 2024

(65) Prior Publication Data

US 2025/0248603 A1 Aug. 7, 2025

(51) Int. Cl.

| | |
|---|---|
| ***A61B 5/00*** | (2006.01) |
| ***A61B 5/02*** | (2006.01) |
| ***A61B 5/021*** | (2006.01) |

(52) U.S. Cl.
CPC ...... *A61B 5/02007* (2013.01); *A61B 5/02125* (2013.01); *A61B 5/7235* (2013.01)

(58) Field of Classification Search
CPC ............ A61B 5/02007; A61B 5/02125; A61B 5/7235; A61B 2562/0204; A61B 5/022
See application file for complete search history.

(56) References Cited

U.S. PATENT DOCUMENTS

| | | | | |
|---|---|---|---|---|
| 10,506,931 | B1 * | 12/2019 | Baruch | A61B 5/02007 |
| 10,973,422 | B2 * | 4/2021 | Pantelopoulos | A61B 5/02416 |
| 12,138,016 | B2 * | 11/2024 | Hocking | A61B 5/02255 |
| 12,364,405 | B1 * | 7/2025 | Androsch | A61B 5/0205 |
| 2006/0079791 | A1 * | 4/2006 | Letremy | A61B 5/6806 600/500 |
| 2006/0173366 | A1 * | 8/2006 | Hasegawa | A61B 5/021 600/500 |
| 2007/0016083 | A1 * | 1/2007 | Hasegawa | A61B 5/02125 600/587 |

(Continued)

FOREIGN PATENT DOCUMENTS

| | | | | |
|---|---|---|---|---|
| WO | WO-2015193917 A2 * | 12/2015 | | A61B 8/5223 |
| WO | WO-2019206818 A1 * | 10/2019 | | A61B 5/02416 |
| WO | WO-2024053380 A1 * | 3/2024 | | A61B 5/02108 |

OTHER PUBLICATIONS

Ryan J. Pewowaruk et al.; "Carotid artery stiffness mechanisms associated with cardiovascular disease events and incident hypertension: the multi-ethnic study of atherosclerosis (MESA)." Hypertension 79, No. 3 (2022): pp. 1 to 19; US.

(Continued)

*Primary Examiner* — May A Abouelela
(74) *Attorney, Agent, or Firm* — Boyle Fredrickson, S.C.

(57) ABSTRACT

A load-dependent component and a structural component of arterial wall stiffness are determined without the need to make measurements of vessel dimensions, for example, using pulse wave velocities, allowing these two components of stiffness to be determined without a skilled sonographer and offering improved treatment and diagnosis of diseases including cardiovascular disease and chronic kidney disease.

19 Claims, 2 Drawing Sheets

(56) References Cited

U.S. PATENT DOCUMENTS

| | | | | |
|---|---|---|---|---|
| 2008/0119741 | A1* | 5/2008 | Friedman | A61B 5/02125 600/485 |
| 2010/0317976 | A1* | 12/2010 | Chelma | A61B 5/021 600/485 |
| 2011/0172546 | A1* | 7/2011 | Komine | A61B 5/021 600/485 |
| 2013/0184595 | A1* | 7/2013 | Mukkamala | A61B 5/7278 600/500 |
| 2013/0184596 | A1* | 7/2013 | Fujii | A61B 5/02125 600/490 |
| 2013/0274620 | A1* | 10/2013 | Zhang | A61B 5/02125 600/490 |
| 2013/0310677 | A1* | 11/2013 | Chiu | A61B 5/02125 600/479 |
| 2013/0310700 | A1* | 11/2013 | Wiard | A61B 5/02007 600/500 |
| 2013/0324859 | A1* | 12/2013 | Park | A61B 5/02007 600/479 |
| 2015/0182132 | A1* | 7/2015 | Harris | A61B 5/7275 340/870.01 |
| 2015/0327786 | A1* | 11/2015 | Lading | A61B 5/7282 600/494 |
| 2016/0120411 | A1* | 5/2016 | Hadley | A61B 5/02055 600/407 |
| 2016/0302672 | A1* | 10/2016 | Kuri | A61B 5/02007 |
| 2016/0345845 | A1* | 12/2016 | Ravid | A61B 5/021 |
| 2017/0079533 | A1* | 3/2017 | Robinson | A61B 5/02116 |
| 2017/0132788 | A1* | 5/2017 | Venugopal | G06T 7/0014 |
| 2017/0354331 | A1* | 12/2017 | Borkholder | G09B 23/288 |
| 2018/0125376 | A1* | 5/2018 | Denney, Jr. | A61B 5/085 |
| 2018/0199824 | A1* | 7/2018 | Centen | A61B 5/0205 |
| 2018/0206734 | A1* | 7/2018 | Lin | A61B 5/02007 |
| 2018/0235567 | A1* | 8/2018 | Bezemer | A61B 5/02007 |
| 2019/0159688 | A1* | 5/2019 | De Groot | A61B 5/6824 |
| 2019/0365256 | A1* | 12/2019 | De Groot | A61B 5/1113 |
| 2020/0129077 | A1* | 4/2020 | Rogers | A61B 5/0004 |
| 2020/0345246 | A1* | 11/2020 | Hilgers | A61B 5/02007 |
| 2021/0145298 | A1* | 5/2021 | Salo | A61B 5/02108 |
| 2021/0204824 | A1* | 7/2021 | Wang | A61B 5/0022 |
| 2021/0236013 | A1* | 8/2021 | Elliott | A61B 5/7435 |
| 2022/0000378 | A1* | 1/2022 | Beutel | A61B 8/02 |
| 2022/0287640 | A1* | 9/2022 | Bikia | A61B 5/7221 |
| 2022/0361761 | A1* | 11/2022 | Beutel | A61B 5/02007 |
| 2023/0034358 | A1* | 2/2023 | Elliott | A61B 5/6844 |
| 2023/0233168 | A1* | 7/2023 | Chen | A61B 5/026 600/424 |
| 2023/0420132 | A1* | 12/2023 | Pahlevan | A61B 5/349 |
| 2024/0032801 | A1* | 2/2024 | Coates | A61B 5/1076 |
| 2025/0152023 | A1* | 5/2025 | Mirota | A61B 5/021 |

OTHER PUBLICATIONS

Sanjiv J. Shah et al.; "Arterial Pulse Wave" MESA Exam 6 Arterial Waveform—Version 1; Manual of Operations; Northwestern University—Feinberg School of Medicine; May 2016; pp. 1 to 17; US.

Matthew J. Budoff et al.; "Clinical applications measuring arterial stiffness: An expert consensus for the application of cardio-ankle vascular index." American journal of hypertension 35, No. 5 (2022): pp. 441-453; US.

* cited by examiner

APPARATUS AND METHOD FOR CHARACTERIZING ARTERIAL STIFFNESS

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to measurement of arterial stiffness and in particular to a system that can separate arterial stiffness into measures of structural stiffness and load-dependent stiffness without requiring difficult measures of arterial dimensions.

Arterial stiffness is strongly associated with elevated risk of cardiovascular disease, kidney disease, cognitive decline, and diabetes. While total arterial stiffness provides important clinical information, the present inventors have determined that arterial stiffness can be usefully decomposed into two components that provide additional insight. The first component, termed structural stiffness, is primarily determined by the structural constituents arterial wall such as elastin and collagen. The second component, termed load-dependent stiffness, relates to a non-linear change in stiffness with loading by blood pressure which stiffens the arterial wall as the arterial wall expands during the cardiac cycle and experiences increased collagen fiber loading.

Studies by the inventors suggest that adults with atypically greater load-dependent stiffness $\gamma$ would benefit from more aggressive medical treatment of cardiovascular disease while patients whose arterial stiffness dominated by structural stiffness would fare better using statin and conventional blood pressure medications. See generally, Pewowaruk R J, Korcarz C, Tedla Y, Burke G, Greenland P, Wu C, Gepner A D, Carotid Artery Stiffness Mechanisms Associated With Cardiovascular Disease Events and Incident Hypertension: the Multi-Ethnic Study of Atherosclerosis (MESA), Hypertension, 2022 March; 79 (3): 659-666, hereby incorporated by reference. Additional studies have established an association between structural stiffness and all-cause mortality and load-dependent stiffness and chronic kidney disease. Total stiffness was associated with dementia but load-dependent and structural stiffness were not. See, Ryan Pewowaruk, Claudia Korcarz, Ian De Boer, Bryan Kestenbaum, Susan R. Heckbert, Yacob G. Tedla and Adam D. Gepner, Carotid Artery Stiffness Mechanisms Are Associated With End Organ Damage and All-Cause Mortality: MESA (Multi-Ethnic Study of Atherosclerosis) originally published 28 Mar. 2023, Journal of the American Heart Association, 2023; 12:e027517, co-authored by the present inventors and incorporated by reference.

Structural stiffness and load-dependent stiffness can be derived from total arterial stiffness, the latter of which can be determined using ultrasonic imaging of the arterial wall. The resulting images provide the arterial diameter at pre-systole and end-diastole and produce a measure of total elasticity when combined with corresponding blood pressure measurements.

Accurate measurement of real-time changes in arterial wall dimension is difficult and requires a skilled medical sonographer who can obtain clear images along the arterial cross-section at systole and diastole as well as an ability to accurately extract dimensions from those images.

SUMMARY OF THE INVENTION

The present inventors have determined that structural and load-dependent stiffness can be obtained without determining arterial dimensions, eliminating the need for skilled real-time imaging. In one embodiment, structural and load-dependent stiffness is extracted from pulse wave measurements of pressure transmitted through the arteries obtained using arterial tonometry.

In one embodiment, the invention provides an apparatus for determination of load-dependent arterial stiffening employing a pressure monitor providing a measure of arterial blood pressure and an arterial pulse wave velocity monitor providing a measure of total arterial stiffness. An electronic processor communicating with the pressure monitor and arterial pulse wave velocity monitor: (a) collects total arterial stiffness values and arterial blood pressures; (b) fits the collected arterial stiffness values and arterial blood pressures to a nonlinear model of arterial elasticity; and (c) provides outputs based on the fit nonlinear model indicating a load-dependent stiffness representing a change in elasticity with arterial distention and a structural stiffness representing an elasticity at a predetermined arterial blood pressure.

It is thus a feature of at least one embodiment of the invention to separate total arterial stiffness into load-dependent and structural components while avoiding the difficult task of measuring arterial distention such as requires either a skilled sonographer or expensive imaging equipment such as an MRI or CT.

The electronic processor may further output a total elasticity providing an elasticity at a patient-specific pressure.

It is thus a feature of at least one object of the invention to provide additional information of total arterial stiffness, for example, relevant with respect to assessing dementia.

The model may provide an arterial distension as an exponential function of arterial blood pressure.

It is thus a feature of at least one embodiment of the invention to provide a tractable model amenable for use without measured arterial dimensions such as would require difficult or expensive imaging.

The structural stiffness may be a model-derived elasticity at a predetermined standard pressure determined from the model.

It is thus a feature of at least one embodiment of the invention to provide a measure that can be compared among patients, for example, having different average blood pressures.

The arterial pulse wave velocity monitor may be an arterial tonometer measuring a velocity of a pressure wave through the artery. The structural stiffness is then a value dependent on pulse wave velocity (PWV) at a predetermined arterial blood pressure ($P_{ref}$).

It is thus a feature of at least one embodiment of the invention to provide the necessary total arterial stiffness measurements using established arterial tonometry.

These particular objects and advantages may apply to only some embodiments falling within the claims and thus do not define the scope of the invention.

DETAILED DESCRIPTION OF THE PREFERRED EMBODIMENT

Figure 1:
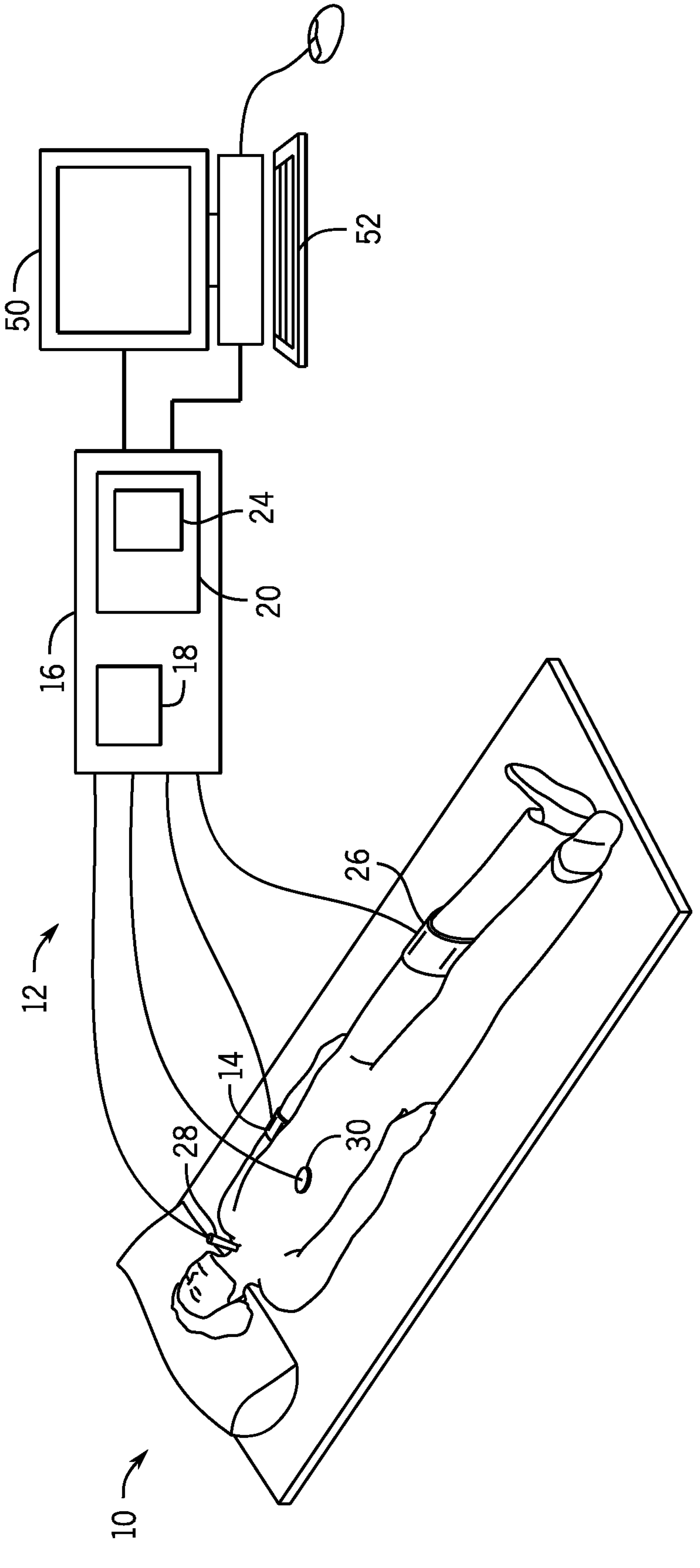
FIG. 1 is a representation of an arterial tonometry system suitable for use with the present invention for collecting pulse wave velocity information and blood pressure data for processing by an electronic computer to provide an output on a display.

Referring now to FIG. 1, an arterial elasticity assessment system 10 per the present invention may make use of a tonometry apparatus 12 that can measure arterial blood pressure and arterial pressure wave velocity.

In one example, the tonometry apparatus 12 provides a brachial cuff 14 providing an inflatable collar for controllably constricting blood flow through the arteries of the arm of a patient and a microphone for detecting oscillometric blood pressure. Values of mean and systolic and diastolic arterial blood pressures are determined by a connected controller 16 receiving cuff pressure and microphone signals.

The controller 16 may have one or more processors 18 communicating with electronic memory 20 holding a stored program 24 applying an empirical formula to the pressure cuff values and microphone signal. As is understood in the art, oscillometric blood pressure monitors measure blood flow sound as the cuff pressure is varied between supra systolic and sub-diastolic pressure values and use an empirical formula to deduce systolic and diastolic pressures. See, for example, Chandrasekhar A, Yavarimanesh M, Hahn J O, Sung S H, Chen C H, Cheng H M, Mukkamala R. Formulas to Explain Popular Oscillometric Blood Pressure Estimation Algorithms, Front Physiol, 2019 Nov. 21; 10:1415, doi: 10.3389/fphys.2019.01415, PMID: 31824333; PMCID: PMC6881246, hereby incorporated by reference.

The controller 16 may also communicate with a femoral cuff 26 and a carotid tonometer 28 each providing sensitive microphones or similar transducers for detecting of a wave shape of a pressure wave in the arteries at the location of the femoral artery and carotid artery. One or more ECG electrodes 30 also communicate with the controller 16 to provide ECG signals from the heart. Together, the femoral cuff 26, carotid tonometer 28, and ECG electrodes 30 allow measurement of a pressure wave velocity from the carotid artery to the femoral artery.

In operation, a measurement is first made of the distance between the femoral cuff 26 and the carotid tonometer 28 by subtracting a distance measured on the patient between the carotid tonometer 28 and the suprasternal notch (SSN) distance and the distance between the SSN and the femoral cuff 26 following the guidelines outlined in the American Heart Association's arterial stiffness scientific statement per: Townsend R R, Wilkinson I B, Schiffrin E L, Avolio A P, Chirinos J A, Cockcroft J R, Heffernan K S, Lakatta E G, McEniery C M, Mitchell G F, Najjar S S, Nichols W W, Urbina E M, Weber T; American Heart Association Council on Hypertension. Recommendations for Improving and Standardizing Vascular Research on Arterial Stiffness: A Scientific Statement From the American Heart Association, Hypertension, 2015 September; 66 (3): 698-722 PMID: 26160955; PMCID: PMC4587661, hereby incorporated by reference.

Measured arrival times of pulse waveforms generated by the heart (detected by the ECG electrodes 30) at each of the femoral cuff 26 and carotid tonometer 28, together with this distance, provide a measure of carotid/femoral pressure wave velocity (PWV) as may be calculated by the controller 16 using the stored program 24. It will be appreciated that similar PWV measurements can be obtained at two points without cuffs and that this example is nonlimiting.

Tonometry apparatus 12 suitable for making the above measurements are available from ATCOR of Naperville, Illinois, USA, under the trade name SphygmoCor® XCEL PWA/PWV when employing a carotid tonometer 28 from Milar, Inc of Houston, Texas, USA, under the trade name SPT-301, the latter providing non-invasive pulse measurements employing a semiconductor sensor having a range from 0 to +300 mmHg.

The controller 16 executing the stored program 24 may use the measurement of PWV and blood pressure to determine measures of structural stiffness and load-dependent stiffness without imaging of the arteries or measurement of artery dimensions. This ability to extract structural stiffness and load-dependent stiffness without direct arterial dimension measurement makes use of the Bramwell-Hill, equation which describes an incompressible fluid (e.g. blood) in an elastic tube (e.g. an artery), relating the measured pulse wave velocity (PWV) to arterial dimensions A and arterial elasticity (dP/dA) as follows:

$$PWV = \sqrt{\frac{1}{\rho} A \frac{dP}{dA}} \tag{1}$$

where

ρ represents the density of the blood (1050 kg/m3);

A is the instantaneous artery lumen cross-sectional area;

P is the instantaneous blood pressure; and

PWV is the pulse wave velocity through the blood vessel measured as discussed above.

The controller 16 employs a model of an artery elasticity as a simple nonlinear exponential function as follows:

$$P = P_d e^{\gamma\left(\frac{A}{A_d}-1\right)} \tag{2}$$

where

P is the instantaneous arterial pressure;

$P_d$ is the pressure at diastole;

γ is a non-linear stiffness parameter to be determined;

A is the instantaneous blood vessel cross-sectional area; and $A_d$ is the blood vessel cross-sectional area at diastole.

The model of equation (2) and the Bramwell-Hill equation (1) may be used to develop a relationship between PWV and stiffness without arterial dimensions as follows: First, differentiating equation (1) yields:

$$\frac{dP}{dA} = \frac{\gamma P_d}{A_d} e^{\gamma\left(\frac{A}{A_d}-1\right)} \tag{3}$$

and substituting the exponential term of equation (1) into (2) yields:

$$\frac{dP}{dA} = \frac{\gamma}{A_d}P \tag{4}$$

Solving (1) for A yields:

$$A = A_d\left[\frac{\ln\left(\frac{P}{P_d}\right)}{\gamma} + 1\right] \tag{5}$$

and combining (4) and (5) provides:

$$A\frac{dP}{dA} = A_d\left[\frac{\ln\left(\frac{P}{P_d}\right)}{\gamma} + 1\right]\frac{\gamma}{A_d}P \tag{6}$$

Simplifying equation (6) produces the expression:

$$A\frac{dP}{dA} = P\left[\gamma + \ln\left(\frac{P}{P_d}\right)\right] \tag{7}$$

The left side of equation (7) can be substituted into equation (1) and simplified to yields:

$$\gamma = \rho\frac{PWV^2}{P} - \ln\left(\frac{P}{P_d}\right) \tag{8}$$

providing the non-linear stiffness parameter $\gamma$ without knowledge of arterial dimensions.

A structural stiffness may be determined by using the model of equation (2) with the computed non-linear stiffness parameter $\gamma$ value at a predetermined standard blood pressure $P_{ref}$, for example, 100 mmHg per the following formula.

$$PWV_{P_{ref}} = \sqrt{\frac{1}{\rho}P_{ref}\left[\gamma + \ln\left(\frac{P_{ref}}{P_d}\right)\right]} \tag{9}$$

The load-dependent stiffness is then calculated as the difference between total stiffness value PWV and the structural stiffness value $PWV_{P_{ref}}$. The structural and load-dependent stiffness values allow ready comparisons among individuals. The total stiffness value is based on the patient's current PWV value and will have some dependency on blood pressure, but the total stiffness value measurement does not require a determination of blood pressure.

Figure 2:
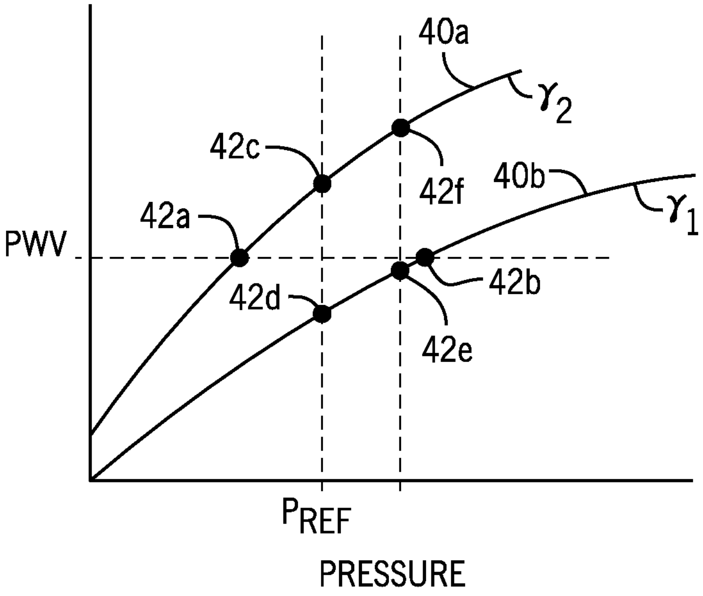
FIG. 2 is a graph depicting modeled arterial elasticity and showing how pulse wave velocity alone can be associated with substantially different arterial conditions and showing a determination of structural stiffness by choosing a common pressure reference.

Referring now to FIG. 2, the additional information provided by structural stiffness $PWV_{P_{ref}}$ and load-dependent stiffness can be seen by modeled elasticity curves 40*a* and 40*b* which distinguish otherwise identical total PWV values 42*a* and 42*b*.

Values 42*c* and 42*d* taken at a reference pressure $P_{ref}$ provide structural stiffness values that can be used to compare structural stiffness among different patients.

Total stiffness values 42*e* and 42*f* may also be obtained being a value of the PWV at a pressure associated with a specific patient, for example, the patient's mean blood pressure.

Figure 3:
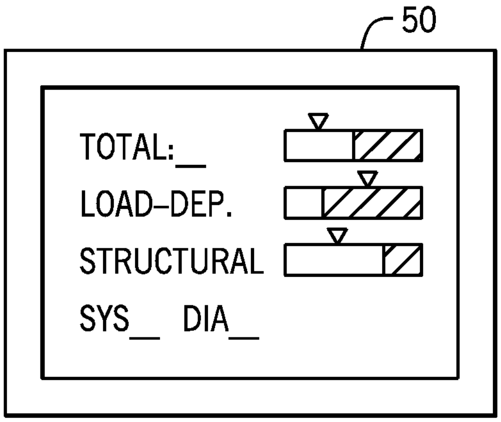
FIG. 3 is an example output display that may be produced by the present invention providing total stiffness as well as structural and load-dependent stiffness information.

The plot of FIG. 2 may be displayed on a monitor 50 attached to the controller 16 (shown in FIG. 1). More typically, and referring to FIG. 3, quantitative and graphical representations of total stiffness, load-dependent stiffness, and structural stiffness may be provided.

The invention contemplates that the program 24 will also have access to other information about the patient and empirical studies related to load-dependent stiffness and structural stiffness so that the graphical representation of total stiffness, load-dependent stiffness, and structural stiffness can place these values within ranges based on the particular patient information and also on a comparison of these values to each other to establish clinical significance. Standard systolic and diastolic pressures may also be provided.

It will be appreciated that other instruments than an arterial tonometer may be used to measure arterial pulse wave velocity including, for example, imaging systems such as ultrasound imaging systems or MRI imaging systems. Such pulse wave velocities may be distinguished from simple sound speed in blood because pulse wave velocities are affected by energy transfer between the elastic deformation of the blood vessel and kinetic energy as opposed to energy transfers between thermodynamic pressure and kinetic energy that controls sounds speed in the blood.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An apparatus for determination of arterial stiffening comprising:

a pressure monitor adapted to provide a measure of arterial blood pressure in a human patient;

a first and second sensor configured to be independently positionable at different locations on the body and adapted to determine an arterial pulse wave velocity to provide a measure of total arterial stiffness; and an electronic processor communicating with the pressure monitor and arterial pulse wave velocity monitor and executing a stored program to:

(a) collect total arterial stiffness values and arterial blood pressures;

(b) fit the collected arterial stiffness values and arterial blood pressures to a nonlinear model of arterial elasticity; and (c) provide outputs, based on the fit nonlinear model, indicating a load-dependent stiffness representing a change in elasticity with arterial distention and a structural stiffness representing the elasticity at a predetermined arterial blood pressure.

2. The apparatus of claim 1 wherein the load-dependent stiffness is determined from a difference between the total stiffness and the structural stiffness.

3. The apparatus of claim 2 wherein the total stiffness is a function of arterial wave velocity at a patient's current blood pressure.

4. The apparatus of claim 1 wherein the first and second sensors are an arterial tonometer measuring an acoustic signal at least one arterial position to determine a velocity of a pressure wave through an artery.

5. The apparatus of claim 4 wherein the arterial tonometer provides measurement of pulse wave velocity at two positions of a carotid artery to a femoral artery.

6. The apparatus of claim 1 wherein the model provides the arterial blood pressure as an exponential function of arterial distention.

7. The apparatus of claim 6 wherein the model is:

$$P = P_d e^{\gamma\left(\frac{A}{A_d}-1\right)}$$

where:

P is the instantaneous arterial pressure;

$P_d$ is the pressure at diastole;

$\gamma$ is a non-linear stiffness;

A is the instantaneous blood vessel cross-sectional area; and $A_d$ is the blood vessel cross-sectional area at diastole; and wherein the model is used to determine the structural stiffness at the predetermined arterial blood pressure.

8. The apparatus of claim 7 wherein the first and second sensors are an arterial tonometer measuring a velocity of a pulse wave through an artery and the structural stiffness is a value dependent on pulse wave velocity (PWV) at a predetermined arterial blood pressure ($P_{ref}$).

9. The apparatus of claim 8 wherein the pressure wave velocity $PWV_{P_{ref}}$ at a predetermined arterial blood pressure ($P_{ref}$) is determined from the model and the non-linear stiffness y according to:

$$PWV_{P_{ref}} = \sqrt{\frac{1}{\rho} P_{ref}\left[\gamma + \ln\left(\frac{P_{ref}}{P_d}\right)\right]}$$

where:

ρ is the density of the blood; and $P_d$ is the pressure at diastole.

10. A method for determination of structural stiffness and load-dependent arterial stiffness employing a pressure monitor adapted to provide a measure of arterial blood pressure in a human patient and a first and second sensor configured to be independently positionable at different locations on the body and adapted to determine an arterial pulse wave velocity to provide a measure of total arterial stiffness, the pressure monitor and arterial pulse wave velocity monitor communicating with an electronic processor operating to: collect total arterial stiffness values and arterial blood pressures; fit the collected arterial stiffness values and arterial blood pressures to a nonlinear model of arterial elasticity; and (a) operate the processor to measure arterial blood pressure and total arterial stiffness;

(b) operate the processor to fit the collected arterial stiffness values and arterial blood pressures to the nonlinear model of arterial elasticity; and (c) operate the processor to output the load-dependent arterial stiffness representing a change in elasticity with arterial distention and the structural stiffness representing an elasticity at a predetermined arterial blood pressure, based on the fit nonlinear model.

11. The method of claim 10 wherein the load-dependent stiffness is determined from a difference between the total stiffness and the structural stiffness.

12. The method of claim 11 wherein the total stiffness value is a function of arterial wave velocity at a patient's current blood pressure.

13. The method of claim 10 wherein the first and second sensors are an arterial tonometer measuring a velocity of a pressure wave through an artery.

14. The method of claim 13 wherein the arterial tonometer provides measurement of pressure wave velocity from a carotid artery to a femoral artery.

15. The method of claim 10 wherein the nonlinear model provides the arterial blood pressure as an exponential function of arterial distention.

16. The method of claim 15 wherein the nonlinear model is:

$$P = P_d e^{\gamma\left(\frac{A}{A_d}-1\right)}$$

where:

P is the instantaneous arterial pressure;

$P_d$ is the pressure at diastole;

$\gamma$ is the non-linear stiffness;

A is the instantaneous blood vessel cross-sectional area; and $A_d$ is the blood vessel cross-sectional area at diastole.

17. The method of claim 15 wherein the structural stiffness is an elasticity at a predetermined standard pressure determined from the nonlinear model.

18. The method of claim 17 wherein the first and second sensors are an arterial tonometer measuring a velocity of a pulse wave through an artery and the structural stiffness is a value dependent on pulse wave velocity (PWV) at a predetermined arterial blood pressure ($P_{ref}$).

19. The method of claim 18 wherein the pressure wave velocity $PWV_{P_{ref}}$ at a predetermined arterial blood pressure ($P_{ref}$) is determined from the model and the non-linear stiffness according to:

$$PWV_{P_{ref}} = \sqrt{\frac{1}{\rho} P_{ref}\left[\gamma + \ln\left(\frac{P_{ref}}{P_d}\right)\right]}$$

where:

ρ is the density of the blood; and $P_d$ is the pressure at diastole.

* * * * *